(12) United States Patent
Stocker

(10) Patent No.: US 8,102,178 B2
(45) Date of Patent: Jan. 24, 2012

(54) DETECTOR ARRANGEMENT

(75) Inventor: Stefan Stocker, Großenseebach (DE)

(73) Assignee: Siemens Aktiengesellschaft, Munich (DE)

( * ) Notice: Subject to any disclaimer, the term of this patent is extended or adjusted under 35 U.S.C. 154(b) by 56 days.

(21) Appl. No.: 12/461,139

(22) Filed: Aug. 3, 2009

(65) Prior Publication Data

US 2010/0026301 A1 Feb. 4, 2010

(30) Foreign Application Priority Data

Aug. 4, 2008 (DE) .................. 10 2008 036 289

(51) Int. Cl.
*G01V 3/00* (2006.01)
(52) U.S. Cl. ....................................... 324/318; 324/322
(58) Field of Classification Search .................. 324/318, 324/322; 250/370.15
See application file for complete search history.

(56) References Cited

U.S. PATENT DOCUMENTS

| | | | |
|---|---|---|---|
| 6,586,744 B1 | 7/2003 | Griesmer et al. | |
| 7,342,234 B2 * | 3/2008 | Yanagita et al. | 250/370.15 |
| 7,488,949 B2 * | 2/2009 | Ueno et al. | 250/370.15 |
| 2005/0067579 A1 | 3/2005 | Ueno et al. | |
| 2007/0080296 A1 | 4/2007 | Ueno et al. | |
| 2010/0006782 A1 * | 1/2010 | Ladebeck | 250/515.1 |

FOREIGN PATENT DOCUMENTS

| | | |
|---|---|---|
| DE | 102006037047 A1 | 2/2008 |
| DE | 102006045399 A1 | 4/2008 |
| DE | 102007009180 A1 | 8/2008 |
| DE | 102007009184 A1 | 8/2008 |
| DE | 102007019296 A1 | 10/2008 |

* cited by examiner

*Primary Examiner* — Louis Arana
(74) *Attorney, Agent, or Firm* — Harness, Dickey & Pierce, P.L.C.

(57) ABSTRACT

A detector arrangement with a plurality of detector units is disclosed, to each of which a data processing unit is assigned. An embodiment of the detector arrangement includes a cooling system with cooling units which are thermoconductively connected to the detector units and data processing units for cooling. The cooling units are connected to a distribution unit by which a coolant may be supplied to the cooling units in parallel.

10 Claims, 2 Drawing Sheets

DETECTOR ARRANGEMENT

PRIORITY STATEMENT

The present application hereby claims priority under 35 U.S.C. §119 on German patent application number DE 10 2008 036 filed Aug. 4, 2008, the entire contents of which are hereby incorporated herein by reference.

FIELD

At least one embodiment of the present invention generally relates to a detector arrangement with a plurality of detector units, to each of which a data processing unit is assigned, comprising a cooling system with cooling units, which are thermoconductively connected to the detector units and data processing units for cooling.

BACKGROUND

Alongside magnetic resonance tomography (MR), in recent years, positron emission tomography (PET) has also become increasingly widespread in medical diagnosis. Whereas MR is an imaging method for displaying structures and slice images in the interior of the body, PET enables the visualization and quantification of metabolic activities in-vivo.

PET uses the particular properties of positron emitters and positron annihilation in order to determine the function of organs or cell areas quantitatively. Thereby, before the examination, the patient is administered appropriate radiopharmaceuticals that are marked with radionuclides. As they decay, the radionuclides emit positrons that interact with an electron after a short distance resulting in so-called annihilation. Two gamma quanta are then created and fly apart from each other in opposite directions (offset by 180°). The gamma quanta are detected by two opposing PET detector modules inside a specific timeframe (coincidence measurement) from which the location of annihilation is determined at a position on the connecting line between these two detector modules.

For detection purposes, the PET detector module must generally cover a major part of the length of the gantry arc. It is divided into detector elements with side lengths of a few millimeters. On detecting a gamma quantum, each detector element generates an event record that specifies the time and the detection location, that is the corresponding detector element. This information is transferred to a fast logic unit and compared. If two events coincide within a maximum time interval, it is assumed a gamma decay process has occurred on the connecting line between the two associated detector elements. The reconstruction of the PET image is performed with the aid of a tomography algorithm, the so-called back projection.

Since MR systems operate with high magnetic fields, it is necessary to use materials compatible therewith within these systems. In particular, when designing PET detectors in combined PET-MR systems, it is necessary to ensure that the detectors are insensitive to magnetic fields.

With combined PET-MR systems, it is known to use lutetium oxyorthosilicate (LSO) as a scintillation crystal for converting the gamma quanta into light and avalanche photodiodes (APDs) for detecting the light. The APDs are connected to preamplifiers. A ring of PET detectors of this kind is arranged inside an MR appliance. This enables MR and PET data records to be recorded simultaneously.

In particular with the commonly used semiconductor amplifiers and semiconductor detectors, the gain depends upon the temperature. Since the components are subjected to temperature fluctuations during operation, cooling is necessary. The temperature of the amplifiers and photodiodes can be controlled by supplying cooled air. When using air with a constant temperature, the temperature of the amplifiers results from the balance of the generated heat and the heat emitted through air via the surfaces of the amplifiers. The cooling can be used in the same fashion for other parts of the detection system.

However, APDs are not subjected to only temperature fluctuations due to their operation. In particular, the proximity to the gradient coil and the excitation coil in the MR system resulting from the compact design represents a heat source acting on the APDs from the outside. The temperature of a gradient coil is typically between 20 and 80° C. during operation. These temperature differences also affect the APDs and hence their gain. The effects of this heat source can only be controlled with difficulty by way of air cooling.

The sensitive electronics in the electronic circuits associated with PET detectors also have to be protected from overheating.

SUMMARY

In at least one embodiment of the present invention, a detector arrangement is disclosed which can be cooled in a simple and efficient manner.

An example embodiment of the invention discloses a detector arrangement with a plurality of detector units, to each of which a data processing unit is assigned. The detector arrangement further comprises a cooling system with cooling units which are thermoconductively connected to the detector units and data processing units for cooling. The cooling units are connected to a distribution unit by which a coolant may be supplied in parallel to the cooling units. Compared to serial cooling, the parallel cooling in the detector arrangement enables simpler and more efficient cooling with which even the slightest temperature fluctuations can be effectively prevented. This is in particular of great importance with PET detectors. In particular, the cooling capacity provided to the parallel cooling units is of an equal magnitude which is something which cannot be guaranteed with serial cooling.

In an advantageous embodiment of the invention, the distribution unit has a geometric shape substantially corresponding to the geometric arrangement of the detector units and data processing units. The adjustment of the geometric shapes of the detector arrangement and the distribution unit enables the cooling system to be implemented in a particularly simple way. This minimizes the length of the coolant flow paths from the distribution unit to the cooling units. The coolant is only divided up shortly before the cooling of the cooling units thus enabling a compact design.

Advantageously, one embodiment of the invention provides that the distribution unit comprises a coolant canal with a cross section dimensioned in such a way that all the cooling units can be supplied uniformly with coolant. This ensures that, even with a plurality of detector units, a sufficient supply of coolant to stabilize the temperature is guaranteed.

In an advantageous embodiment of the invention, the distribution unit consists at least partially of a highly thermoconductive material which is in thermal contact with the coolant and the data processing units are arranged in such a way that they are in thermal contact with the highly thermoconductive material. In this embodiment of the invention, the data processing units can be efficiently cooled by direct contact with the distribution unit so that only the detector units are connected to the cooling units and cooled by them.

Advantageously, in one embodiment of the invention, the distribution unit comprises a holding fixture which is mechanically connected to the detector units and/or the data processing units so as to ensure that they are held in their relevant positions. This embodiment also enables a compact design of the detector arrangement. A separate holding fixture for the detector units and the data processing units is not necessary.

BRIEF DESCRIPTION OF THE DRAWINGS

Further advantages and embodiments of the invention emerge from the following descriptions of example embodiments with reference to the diagrams, which show.

DETAILED DESCRIPTION OF THE EXAMPLE EMBODIMENTS

Figure 1:
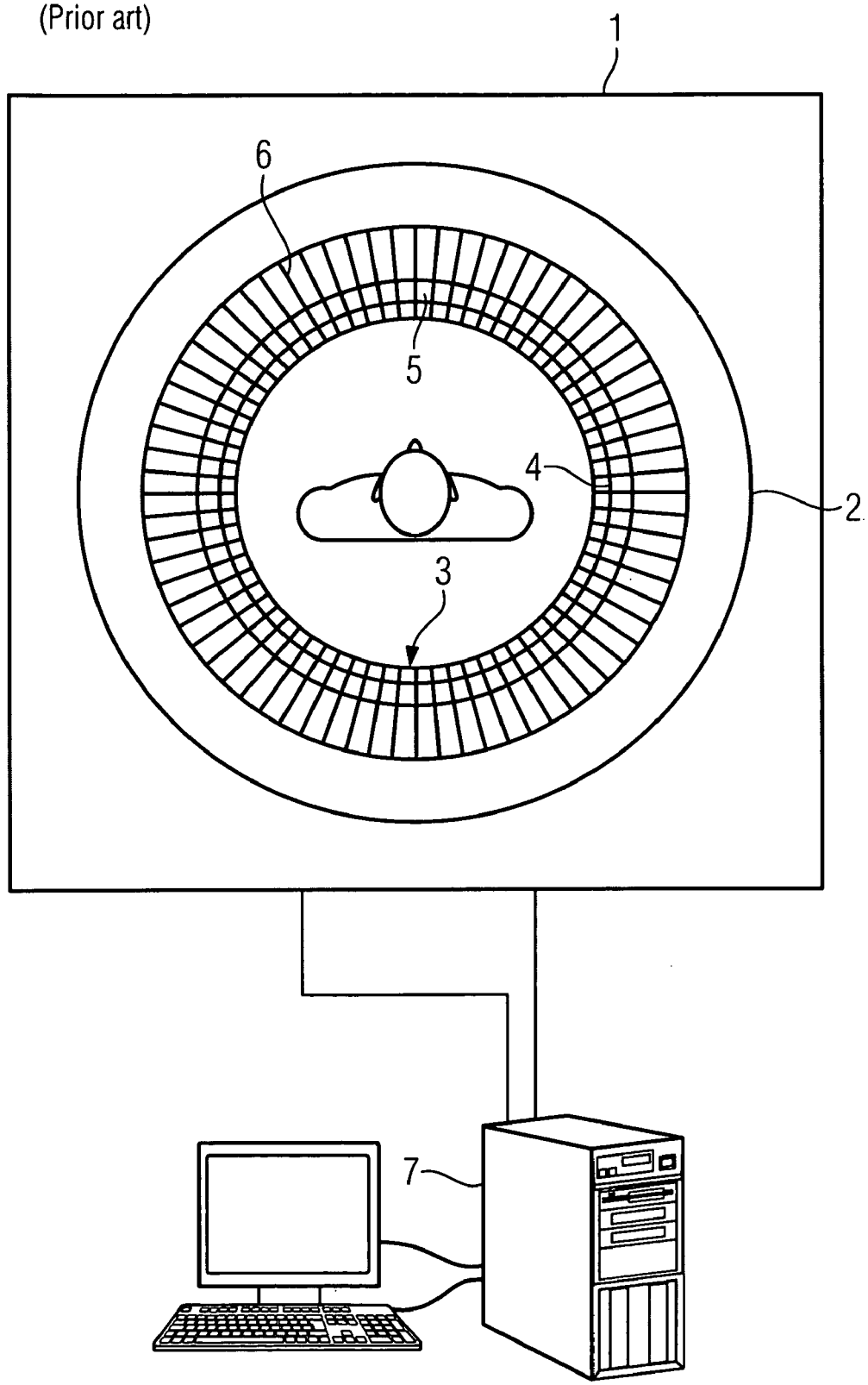
FIG. 1 a known embodiment of an MR-PET appliance,
FIG. 2 a schematic wiring diagram of a cooling unit,
FIG. 3 an embodiment of a distribution unit,
FIG. 4 an alternative embodiment of the distribution unit and
FIG. 5 a further alternative embodiment of the distribution unit.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used on a combined MR-PET appliance. A combined appliance has the advantage that both MR and PET data can be acquired isocentrically. This allows precise definition of the examination volume within the region of interest from the data of the first modality (PET) and the use of this information in the further modality (e.g. magnetic resonance). Although transfer of the volume information of the region of interest from an external PET appliance to an MR appliance is possible, this requires increased complexity to register the data. In general, all data which can be determined with magnetic resonance or other imaging methods can be determined in the region of interest selected in the PET data record. For example instead of spectroscopy data, it is also possible to acquire fMR data, diffusion maps, T1 or T2-weighted images or quantitative parameter maps by means of magnetic resonance examinations in the region of interest. It is also possible to use methods from computed tomography (e.g. perfusion measurement, multi-energy imaging) or X-rays. In each case, it is advantageous with the described method that the region of interest can be restricted very selectively to a specific pathology present in the patient by means of the PET data record.

However, in addition, it is also possible to display different biological properties in the PET data record by using a plurality of so-called tracers and hence further to optimize the region of interest and the volume defined in this way or to select a plurality of different examination volumes at the same time, which are then analyzed in subsequent examinations.

FIG. 1 shows a known apparatus 1 for superposed MR and PET imaging. The apparatus 1 comprises a known MR tube 2. The MR tube 2 defines a longitudinal direction z, which extends orthogonally with respect to the plane of the drawing in FIG. 1.

As shown in FIG. 1, a plurality of PET detector units 3 arranged in pairs opposite each other about the longitudinal direction z are arranged coaxially within the MR tube 2. The PET detector units 3 preferably comprise an APD photodiode array 5 with an upstream array of LSO crystals 4 and an electrical amplifier circuit (AMP) 6. However, the invention is not restricted to PET detector units 3 with the APD photodiode array 5 and the upstream array of LSO crystals 4; rather, other types of photodiodes, crystals and apparatuses can be used for detection.

The image processing for superposed MR and PET imaging is performed by a computer 7.

The MR tube 2 defines a cylindrical first field of view along its longitudinal direction z. The plurality of PET detector units 3 defines a cylindrical second field of view along the longitudinal direction z. According to the invention, the second field of view of the PET detector units 3 substantially corresponds to the first field of view of the MR tube 2. This is implemented by a corresponding adaptation of the arrangement density of the PET detector units 3 along the longitudinal direction z.

Figure 2:
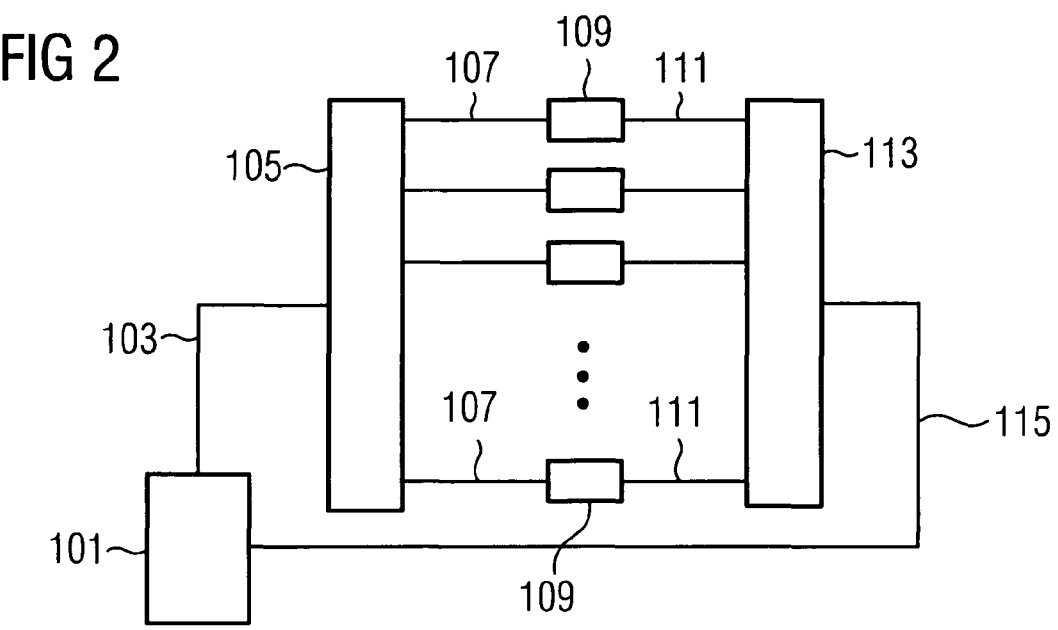

FIG. 2 is a schematic view of an equivalent flowchart of a coolant circuit for an example embodiment of the invention. It includes a coolant source 101, in which, for example, water or another cooling liquid is cooled as a coolant. The coolant source 101 is connected via a coolant delivery line 103 to a preliminary manifold 105. The preliminary manifold 105 is connected by interconnecting lines 107 to heat sinks 109, each of which are assigned to the components of the detector arrangement not shown here. Here, they are in thermal contact with PET detector units and data processing units, which are not shown here. The heat sinks 109 are connected by further interconnecting lines 111 to a return manifold 113. The return manifold 113 brings the interconnecting lines 111 together and connects them to the coolant source 101 on a return line 115. Returned coolant is cooled again in the coolant source 101 and fed via the coolant delivery line 103 into the preliminary manifold 105.

Similarly to the PET detector units and the assigned data processing units, in an example embodiment of the invention, the heat sinks 109 are arranged in a circle around a patient opening in a PET or MR-PET system. The use of the preliminary manifold 105 and the return manifold 113 makes it possible for the entire cooling system to have a compact design. The parallel guidance of the interconnecting lines 107 and 111 means all heat sinks 109 are supplied with coolant of the same temperature. This would not be guaranteed with a serial flow of the coolant through the heat sinks 109 in succession, since it heats up when flowing through each of the heat sinks 109 due to the absorption of energy from the respective heat sinks 109. In the case of a serially arranged coolant circuit, therefore, the last of the heat sinks 109 is provided with much hotter coolant than the first of the heat sinks 109. This results in nonuniform operating temperatures of the PET detector units and data processing units. This problem is avoided by the parallel arrangement of the interconnecting lines 107 and 111 and the heat sinks 109.

The preliminary manifold 105 and the return manifold 113 are preferably ring-shaped or C-shaped and are made of a material with good thermoconductivity, such as, for example, copper. The preliminary manifold 105 and the return manifold 113 each have a channel for receiving the coolant with a flow cross section which is large enough to supply the large number of parallel heat sinks 109 with sufficient coolant. At the same time, the preliminary manifold 105 or the return manifold 113 can also function as heat sinks and be directly in thermal contact with one or more PET detector units or data processing units. In these cases, the lines 107 and 111 and the respective heat sinks 109 are omitted. This facilitates a compact design.

In an alternative embodiment of the invention, the preliminary manifold 105 and the return manifold 113 can simultaneously be used as holding fixtures for PET detector units and/or data processing units. This further reduces the installation size of the cooling system.

A particularly advantageous aspect of the described example embodiments of the invention is the fact that the design of the parallel coolant circuits to the individual heat sinks 109 results in only a slight pressure loss in the system. With a serial arrangement of the coolant circuits, the pressure loss would be much higher making it necessary to work with a higher pressure. It is also possible in a simple way to remove individual PET detector units from the heat sinks 109, for maintenance for example, without this affecting the rest of the system. The parallel cooling circuits are not affected by the removal of one or more PET detector units.

Figure 3:
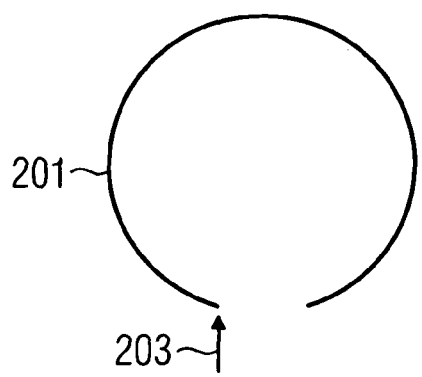

FIG. 3 shows a schematic view of a C-shaped water manifold 201. A coolant may be supplied to one side of the water manifold 201 as indicated by the arrow 203. From the water manifold 201, cooling lines (not shown here) go to detector units to be cooled, for example perpendicular to the plane of the drawing. The corresponding return manifold in which the cooling water is collected again can have a similar arrangement.

Figure 4:
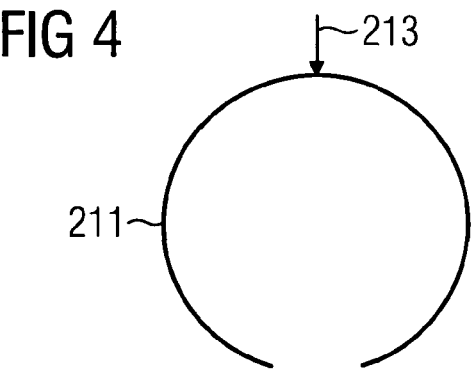

FIG. 4 shows an alternative embodiment of a C-shaped water manifold 211. This embodiment of the water manifold 211 has an inlet for coolant which is disposed in the centre. This is indicated by the arrow 213. In the corresponding return manifold, after passing through, the coolant can be returned to the coolant circuit at the two bottom ends.

Figure 5:
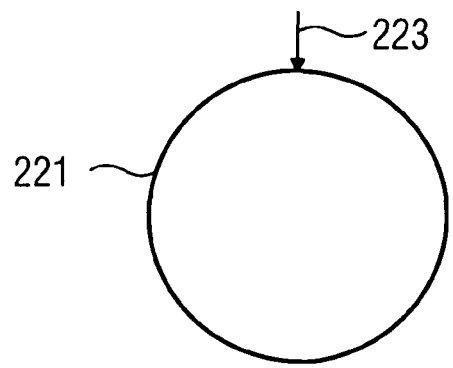

FIG. 5 shows a further alternative embodiment of a water manifold 221. This water manifold has a circular shape and similarly to the embodiment in FIG. 4 has a central inlet. This is indicated by the arrow 223. The outlet of the corresponding return manifold can also be arranged on the opposite side.

The water manifolds shown in FIGS. 3 to 5 are only example embodiments. Numerous other embodiments of the water manifolds are possible according to the most favorable geometry. Preferably, the water manifolds are also used as heat sinks for electronic components. Thereby, the components to be cooled are arranged in such a way that they are in thermal contact with the water manifold.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector arrangement including a plurality of detector assemblies, each detector assembly comprising a detector unit and an associated data processing unit, the detector arrangement comprising:
    a cooling system, including:
        a distribution unit that distributes a coolant, the distribution unit having at least one of a C-shaped configuration and a ring-shaped configuration,
        a plurality of cooling units connected in parallel to the distribution unit such that the coolant is distributed in parallel to the cooling units,
        wherein at least one of the detector assemblies is in direct contact to a respective cooling unit and in contact with at least one of the C-shaped and the ring-shaped distribution unit.

2. The detector arrangement as claimed in claim 1, wherein the distribution unit has a geometric shape which substantially corresponds to a geometric arrangement of at least one of the detector units and the data processing units.

3. The detector arrangement as claimed in claim 1, wherein the distribution unit comprises a coolant canal, and a cross section of the coolant canal is dimensioned such that all the cooling units are uniformly suppliable with coolant.

4. The detector arrangement as claimed in claim 1, wherein the distribution unit comprises a thermoconductive material which is in thermal contact with the coolant and the data processing units are arranged such that the data processing units are in thermal contact with the thermoconductive material.

5. The detector arrangement as claimed in claim 1, wherein the distribution unit comprises a holding fixture connected mechanically to at least one of the detector units and the data processing units such that the at least one of the detector units and the data processing units are held in their respective position.

6. The detector arrangement as claimed in claim 1, wherein the detector units are arranged in a ring shape and the distribution unit is ring-shaped.

7. The detector arrangement as claimed in claim 2, wherein the distribution unit comprises a coolant canal, and a cross section of the coolant canal is dimensioned such that all the cooling units are uniformly suppliable with coolant.

8. The detector arrangement as claimed in claim 2, wherein the distribution unit comprises a thermoconductive material which is in thermal contact with the coolant and the data processing units are arranged such that the data processing units are in thermal contact with the thermoconductive material.

9. The detector arrangement as claimed in claim 2, wherein the distribution unit comprises a holding fixture connected mechanically to at least one of the detector units and the data processing units such that the at least one of the detector units and the data processing units are held in their respective position.

10. The detector arrangement as claimed in claim 2, wherein the detector units are arranged in a ring shape and the distribution unit is ring-shaped.

* * * * *